(12) United States Patent
Thomas et al.

(10) Patent No.: US 6,604,001 B2
(45) Date of Patent: Aug. 5, 2003

(54) IMPLANTABLE CARDIAC RHYTHM MANAGEMENT DEVICE INCORPORATING A PROGRAMMABLE WATCHDOG TIMER

(75) Inventors: Brian P. Thomas, Lakeville, MN (US); Doug M. Birkholz, Shoreview, MN (US); Grant Corcoran, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 309 days.

(21) Appl. No.: 09/812,159

(22) Filed: Mar. 19, 2001

(65) Prior Publication Data

US 2002/0133207 A1 Sep. 19, 2002

(51) Int. Cl.[7] .................................................. A61N 1/37
(52) U.S. Cl. ............................................. 607/27; 607/9
(58) Field of Search ................................ 607/9, 17, 18, 607/27, 28, 30, 31, 60; 600/508, 515, 516, 517; 710/100, 107, 113, 118, 260; 712/248; 713/322, 323, 501

(56) References Cited

U.S. PATENT DOCUMENTS

| | | | |
|---|---|---|---|
| 4,527,568 A | * 7/1985 | Rickards | 607/18 |
| 4,987,529 A | 1/1991 | Craft et al. | 710/113 |
| 5,036,334 A | 7/1991 | Henderson et al. | 342/460 |
| 5,334,222 A | * 8/1994 | Salo et al. | 607/17 |
| 5,418,968 A | 5/1995 | Gobeli | 710/260 |
| 5,471,625 A | 11/1995 | Mussemann et al. | 713/322 |
| 5,607,458 A | * 3/1997 | Causey et al. | 607/27 |
| 5,694,444 A | 12/1997 | Bagchi et al. | 377/54 |
| 5,805,909 A | 9/1998 | Diewald | 713/322 |
| 6,032,248 A | 2/2000 | Curry et al. | 712/37 |
| 6,108,577 A | * 8/2000 | Benser | 600/515 |
| 6,115,636 A | * 9/2000 | Ryan | 607/60 |
| 6,366,810 B1 | * 4/2002 | Johnson et al. | 607/9 |
| 6,427,084 B2 | * 7/2002 | Baker et al. | 607/9 |

* cited by examiner

Primary Examiner—Willis R. Wolfe
(74) Attorney, Agent, or Firm—Thomas J. Nikolai; Nikolai & Mersereau, P.A.

(57) ABSTRACT

A cardiac rhythm management device incorporates a programmable Watchdog timer that permits more stringent time constraints to be placed upon the execution of software/firmware strings during a design phase when a deterministic model is being created. Thus, when performing real-time system engineering analysis on the model, potential imperfections in the deterministic model can be captured and resolved, resulting in a more reliable CRMD that is less likely to electronically reset once implanted in a patient.

5 Claims, 2 Drawing Sheets

IMPLANTABLE CARDIAC RHYTHM MANAGEMENT DEVICE INCORPORATING A PROGRAMMABLE WATCHDOG TIMER

BACKGROUND OF THE INVENTION

I. Field of the Invention

This invention relates generally to implantable cardiac rhythm management devices incorporating a microprocessor-based controller, and more particularly to a microprocessor-based controller incorporating a Watchdog timer whose time-out period is programmable to facilitate deterministic modeling of worse case performance during design testing of the device.

II. Discussion of the Prior Art

State-of-the-art cardiac rhythm management devices, including bradycardia pacemakers, anti-tachycardia pacemakers and defibrillators typically incorporate microprocessor-based controllers capable of accepting input information from physiologic sensors and for providing therapy through timed application of cardiac stimulating pulses to the heart when sensed conditions dictate. The software/firmware executed by the microprocessor typically involve a large plurality of multi-tasking operations being executed in a real-time mode. As such, various events are carried out asynchronously and, frequently, multiple events happen concurrently. Thus, the time required to execute a certain function can vary significantly. Variations in the electronic circuitry itself can also result in variations in the length of time required to execute certain tasks. Then, too, variations in the system clock circuitry that drives the microprocessor can also cause variation in the length of time it takes to execute a given function.

Efforts of development engineers working on CRMD designs to arrive at an accurate deterministic model of the device's performance are necessarily adversely impacted by such variations. For this reason, the microprocessor embodies a so-called Watchdog timer which is a circuit that is used to insure that the device meets time requirements and to cause a system reset in the event of a system failure occurring because an instruction string is not executed within specified time constraints. Watchdog timers heretofore used in CRMDs of which we are aware have a fixed time-out period of, for example, 32 ms, set by hard-wired circuit components. The software/firmware being executed provides for the delivery of an interrupt signal to the Watchdog timer, which is used to reset the Watchdog timer. Such interrupt signals are designed to be delivered at intervals shorter than the fixed time-out period established for the Watchdog timer. If due to asynchronous events or variations in hardware, the time to execute a software or firmware string becomes excessive and no interrupt is generated to reset the Watchdog timer before expiration of its fixed time-out period, the Watchdog circuit will reset the microprocessor to escape the error condition and to restart the device with its default values.

System resets by the Watchdog timer are to be avoided once the device has been implanted. For example, if a patient should be experiencing an episode of ventricular fibrillation, it is important that the CRMD deliver a cardioverting shock on a timely basis and that the device not suffer a Watchdog reset at this critical moment and thereafter undergo reinitiation before the shock can be delivered. Reinitiation can take a minute or more and during this time therapy is being withheld. It is, therefore, very important that, following implant, a combination of events involving either hardware, software or firmware come into play to extend the time for execution of a software or firmware defined function beyond the time-out period of the Watchdog timer employed.

During development of microprocessor-based CRMDs, when development engineers are creating a deterministic model of how long a given function will take to execute, it would be beneficial to have a Watchdog timer whose time-out period can be programmed in, rather than being fixed in length. Then, the period of the Watchdog timer could be set to a shortened value and if it is found that a given function executes in the shortened period, it is all but guaranteed that it will execute in a longer period set into the Watchdog timer at the time of final testing and prior to its being furnished to the implanting surgeon.

It is accordingly an object of the present invention to provide a CRMD having a programmable Watchdog timer for detecting fault conditions in hardware, software and/or firmware where the time-out period of the Watchdog timer can be programmed to any of a plurality of predetermined time intervals.

SUMMARY OF THE INVENTION

In accordance with the present invention, the foregoing objects are attained by providing a CRMD of a type having a sensing circuit for detecting cardiac depolarization events, a pulse generator for delivering cardiac stimulating pulses to the heart and a microprocessor-based controller that is coupled to receive electrical signals from the sensor and where the microprocessor-based controller is connected in controlling relation to the pulse generator. The microprocessor-based controller operates to execute a program of instructions stored therein so as to produce control signals at timed intervals to the pulse generator based, at least in part, on the electrical signals from the sensor. The microprocessor-based controller also incorporates a Watchdog timer for monitoring instruction execution time by the microprocessor-based controller with the Watchdog timer being capable of producing a flag signal when more than a predetermined period of time has been required for executing one or more instructions in the program. The Watchdog timer of the present invention is programmable, allowing its time-out period to be readily changed. This allows a first time-out period to be used during system design and a second, longer time-out period to be programmed in at the time of post-manufacture testing. If the Watchdog timer does not produce flag signals when operating with its shorter time-out period, it is highly unlikely that such flag signals would occur with the longer time-out period that is programmed in at a point in time prior to implantation of the device in the patient.

DESCRIPTION OF THE DRAWINGS

The foregoing objects, features and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
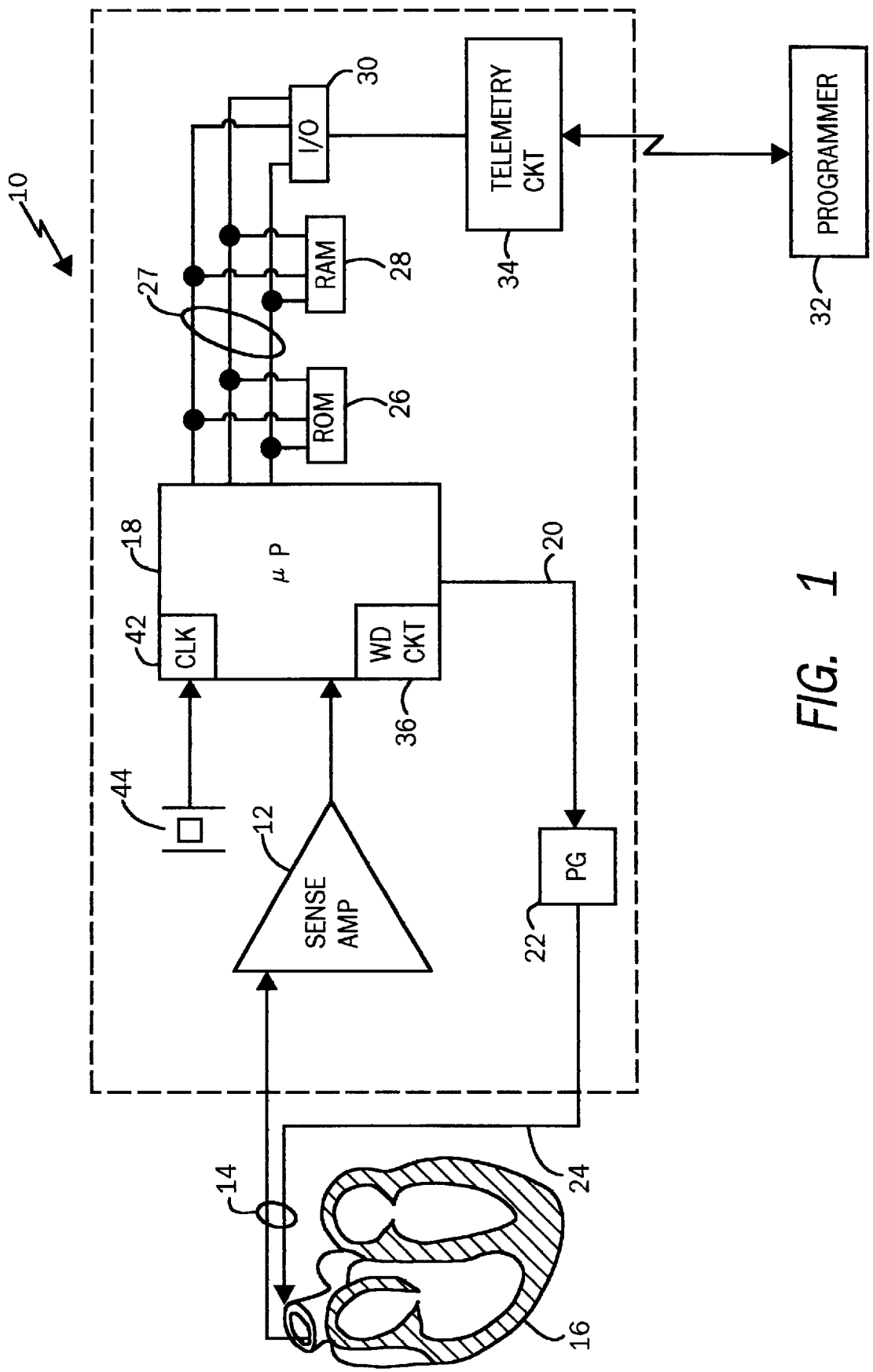
FIG. 1 is a block diagram representation of a CRMD in which the present invention finds use.

FIG. 1 illustrates, by means of a block diagram, a typical cardiac rhythm management device in which the present invention finds use. It may comprise a bradycardia pacemaker, either single chamber or dual chamber, an anti-tachycardia pacer or an implantable defibrillator. The device is indicated generally by numeral 10 and is seen to include a sense amplifier circuit 12 that is coupled by a conventional pacing defibrillating lead 14 having one or more electrodes (not shown) that engage cardiac tissue 16. The sense amplifier is arranged to detect cardiac depolarization signals while discriminating against noise and other artifacts. The output from the sense amplifier is applied as an input to a microprocessor 18 whose output on line 20 controls a pulse generator 22 that is adapted to apply cardiac stimulating pulses over a conductor 24 in the lead 14 to the heart 16.

The microprocessor 18 includes a read-only memory (ROM) 26 that is adapted to store a program of instructions executable by the microprocessor 18 and a random access memory (RAM) 28 that is adapted to store programmable parameters and intermediate operands generated by the microprocessor 18 during execution of its program. Also connected to the bus 27 is an input/output controller 30, allowing two-way communication with an external programmer 32, via a telemetry circuit 34.

The implantable CRMD 10 is designed to operate in both a TEST mode and in a NORMAL mode. The device is programmed to its normal mode prior to shipment from the factory to an implanting surgeon or hospital. The Watchdog circuit 36 implemented within the microprocessor 18 is programmable only when the device 10 is in its TEST mode. That is to say, its parameters can only be changed at the factory and are not accessible for change by a medical professional.

Figure 2:
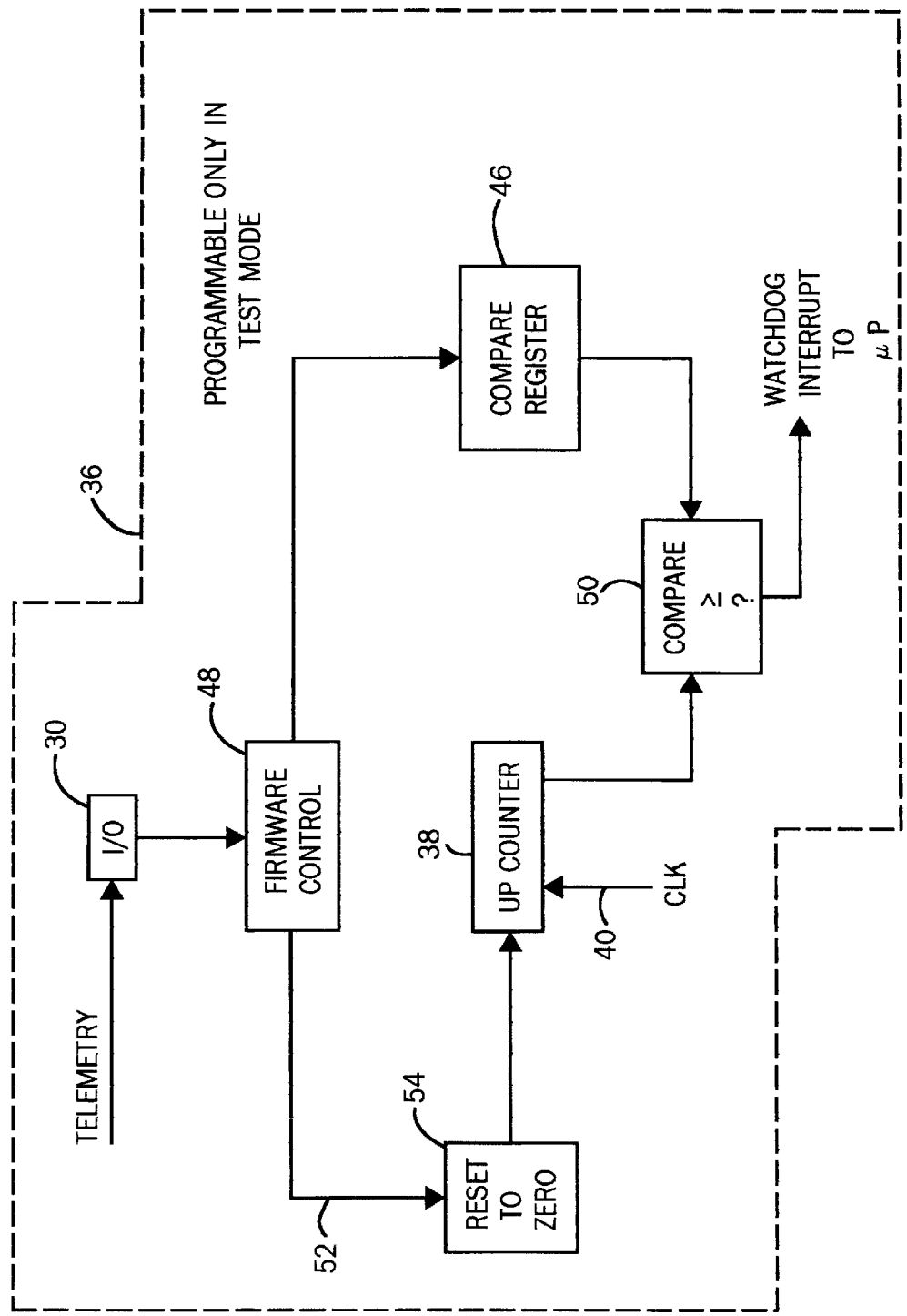
FIG. 2 is a general block diagram of a Watchdog timer embodied in the microprocessor-based controller of FIG. 1.

FIG. 2 is a general block diagram of the Watchdog timer 36 embodied in the microprocessor-based controller 18 of FIG. 1. It includes an up-counter 38 that is connected to receive regularly occurring clock pulses, via line 40, from the clock circuit 42 whose frequency is controlled by a crystal 44 (FIG. 1). The Watchdog circuit 36 further includes a compare register 46 which, during the TEST mode can be programmed, via the telemetry link, the I/O controller 30, the firmware control module 48, to contain a predetermined value defining the time-out period for the Watchdog circuit. The output from the up-counter 38 and from the compare register 46 are compared at block 50 and when the up-counter 38 accumulates a count equal to or greater than the predetermined number stored in the compare register 46, the compare block 50 outputs a Watchdog Interrupt to the microprocessor.

Under firmware control 48, however, a signal is sent over line 52 and block 54 to reset the up-counter to zero. The firmware or software includes an instruction in a string of instructions that causes the block 54 to issue a reset to the up-counter 38. The periodicity of successive reset instructions is variable due to the nature of the execution of the software routine scheduled entries, but this periodicity is significantly less than the time-out period of the Watchdog's maximum duration established by the contents of the compare register 46. Thus, it is only if there is a problem with the hardware or software of the device 10 that delays the delivery of counter reset signals to the counter 38 that its contents will ever reach the number contained in the compare register 46 to cause the compare block 50 to generate a Watchdog Interrupt to the microprocessor.

In accordance with the present invention, the number entered into the compare register 46 is a programmable parameter when the device 10 is operating in its TEST mode. This allows development engineers responsible for debugging the hardware and software to enter a time value in the compare register 46 that is shorter than the time value which is later programmed into the compare register 46 just before exiting the TEST mode for the device. Accordingly, if the software/firmware is exercised with a shortened time-out period, it is highly probable that no Watchdog Interrupts will be generated once the contents of the compare register 46 are programmed to define the time-out period for the Watchdog when the device 10 is operating in its NORMAL mode.

In the event of a programming error or hardware/firmware fault condition, the up-counter 38 may not be reset before its count value reaches the contents of the compare register 46, resulting in a Watchdog Interrupt to the microprocessor which generally results in a restart of the microprocessor-based controller 18 or other remedial action in an attempt to clear the fault condition.

By replacing the fixed time constant Watchdog circuit of the prior art with the present invention that allows programming of the Watchdog's time-out period, various ones of the reliability issues and challenges faced by system's engineers and firmware engineers attempting to perform deterministic, real-time evaluation of the CRMD design can be better accommodated. By performing system tests with more stringent time restrictions imposed, the frequency of Watchdog resets being generated, post-implant, are reduced. However, appropriate Watchdog resets, such as when the embedded software/firmware has an error that went undetected during the testing process, can still occur. Inappropriate Watchdog resets, such as when the software/firmware is not in an error condition and the device is trying to perform its intended life-saving functions, but because of some combination of external factors, the Watchdog resets the microprocessor are reduced.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac rhythm management device comprising means for sensing cardiac depolarization events; pulse generating means for delivering cardiac stimulating pulses to the heart; a microprocessor-based controller coupled to receive the electrical signals from the sensing means and connected in controlling relation to the pulse generating means, the microprocessor-based controller executing a program of instructions stored therein for producing control signals at timed intervals to the pulse generating means based, at least in part, on the electrical signals from the sensing means; and a Watchdog timer in the microprocessor-based controller for monitoring instruction execution time by the microprocessor-based controller and capable of producing a Watchdog Interrupt signal when more than a predetermined period of time is required for executing one or more instructions in said program, the length of the predetermined time period being a programmable parameter.

2. The cardiac rhythm management device of claim 1 wherein the microprocessor-based controller has a normal mode and a test mode, the predetermined period of the Watchdog timer being programmable only when the microprocessor-based controller is in said test mode.

3. A method of debugging an implantable rhythm cardiac management device of the type incorporating a microprocessor-based controller and a pulse generator controlled by said microprocessor-based controller, the microprocessor configured to execute a program of instructions within predetermined time constraints, comprising the steps of:

(a) providing a counter that is coupled to receive regularly occurring clock signals from the microprocessor-based controller;

(b) including in the program of instructions counter reset instructions at predetermined points in a sequence of the instructions;

(c) resetting the counter upon execution of the counter reset instructions; and (d) continuously comparing quantities contained in the counter with a first predetermined value for equality and generating an interrupt signal for reinitiating the microprocessor-based controller when the comparison obtains, said predetermined value being a programmable parameter.

4. The method of claim 3 wherein the first predetermined value is programmable only when the cardiac rhythm management device is in a test mode.

5. The method of claim 4 and further including the step of reprogramming the first predetermined value to a second predetermined value greater than the first predetermined value at the conclusion of operation in the test mode.

* * * * *